United States Patent
Tsai

(10) Patent No.: US 8,001,855 B2
(45) Date of Patent: Aug. 23, 2011

(54) FLUID TRANSFERRING APPARATUS

(75) Inventor: Ying-Lan Tsai, Bade (TW)

(73) Assignee: MEDI Medical Engineering Corp., Bade, Taoyuan County (TW)

( * ) Notice: Subject to any disclaimer, the term of this patent is extended or adjusted under 35 U.S.C. 154(b) by 847 days.

(21) Appl. No.: 12/007,663

(22) Filed: Jan. 14, 2008

(65) Prior Publication Data

US 2009/0178497 A1    Jul. 16, 2009

(51) Int. Cl.
*G01N 1/22*    (2006.01)
(52) U.S. Cl. .................................................. 73/863.11
(58) Field of Classification Search .................. None
See application file for complete search history.

(56) References Cited

U.S. PATENT DOCUMENTS

| | | | |
|---|---|---|---|
| 4,806,316 A | 2/1989 | Johnson et al. | |
| 5,478,751 A * | 12/1995 | Oosta et al. | 436/165 |
| 5,912,134 A * | 6/1999 | Shartle | 435/7.24 |
| 7,097,811 B2 | 8/2006 | Yao et al. | |
| 7,125,711 B2 * | 10/2006 | Pugia et al. | 435/288.5 |
| 7,138,269 B2 | 11/2006 | Blankenstein et al. | |
| 7,220,385 B2 | 5/2007 | Blecka et al. | |
| 2003/0166265 A1* | 9/2003 | Pugia et al. | 435/288.3 |
| 2007/0025875 A1* | 2/2007 | Peters et al. | 422/57 |

* cited by examiner

*Primary Examiner* — Robert Raevis
(74) *Attorney, Agent, or Firm* — Muncy, Geissler, Olds & Lowe, PLLC

(57) ABSTRACT

A fluid transferring apparatus includes a frame, a sample inlet chamber, a filling channel, a plurality of filling passageways, a plurality of test wells, and a plurality of venting passageways. The sample inlet chamber is disposed within the frame. The filling channel is disposed on the frame and connected to the sample inlet chamber, wherein the filling channel has a top part above the outlet of the sample inlet chamber. The filling passageways are disposed on the frame and connected to the filling channel. The test wells are disposed within the frame and connected to the filling passageways respectively, wherein the test wells are below the top part of the filling channel. The venting passageways are connected to the test wells respectively.

19 Claims, 3 Drawing Sheets

FLUID TRANSFERRING APPARATUS

BACKGROUND

1. Field of Invention

The present invention relates to a fluid transferring means. More particularly, the present invention relates to an apparatus having means for volumetrically transferring a sample fluid.

2. Description of Related Art

The concentration of analytes in blood in many cases must be monitored regularly. This is especially the case when regular drug treatment is required in relation to the concentration of the particular substance. The most important example is diabetes. Patients with diabetes should constantly monitor their blood-glucose level to match their insulin injections to their need at the time and thereby keep their blood-glucose levels within specified limits.

Laboratory biochemical analyses are often carried out to obtain the concentration of analytes in blood or other fluid samples. However, such laboratory biochemical analyses are not available for patients or users who are not familiar with chemical techniques. Even if the laboratory biochemical analyses were carried out by the patients or users, the result would be unreliable due to their poor pipetting technique. Moreover, since it becomes more and more important for the determination of multiple biomarkers simultaneously by a simple and reliable means, the process will be more difficult and complicated when users must deal with multiple markers analysis. Therefore, there is a need for a fluid transferring apparatus to replace the complex pipetting operation in many biochemical analyses.

SUMMARY

According to one embodiment of the present invention, a fluid transferring apparatus includes a frame, a sample inlet chamber, a filling channel, a plurality of filling passageways, a plurality of test wells, and a plurality of venting passageways. The sample inlet chamber is disposed within the frame. The filling channel is disposed on the frame and connected to the sample inlet chamber, wherein the filling channel has a top part above the outlet of the sample inlet chamber. The filling passageways are disposed on the frame and connected to the filling channel. The test wells are disposed within the frame and connected to the filling passageways respectively, wherein the test wells are below the top part of the filling channel. The venting passageways are connected to the test wells respectively.

According to another embodiment of the present invention, a fluid transferring apparatus includes a frame, a sample inlet chamber, a filling channel, a pump, a plurality of filling passageways, a plurality of test wells, and a plurality of venting passageways. The sample inlet chamber is disposed within the frame. The filling channel is disposed on the frame and connected to the sample inlet chamber, wherein the filling channel has a top part. The pump pumps a sample fluid from the sample inlet chamber over the top part of the filling channel. The filling passageways are disposed on the frame and connected to the filling channel. The test wells are disposed within the frame and connected to the filling passageways respectively, wherein the test wells are below the top part of the filling channel. The venting passageways are connected to the test wells respectively.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

There have been various gravity-driven fluid transferring apparatuses applied in many biochemical analysis processes to reduce the manipulations required for the fluid specimen. However, those gravity-driven fluid transferring apparatuses have one common problem, which is, the timing of when the fluid specimen is filled into the fluid transferring apparatus cannot be exactly obtained because the filling operation is usually manual and complex. Uncertain filling timing results in uncertain reaction time, and thus the analysis result will be unreliable. Accordingly, the following embodiment of the present invention will provide a solution to the above-mentioned problem.

Figure 1:
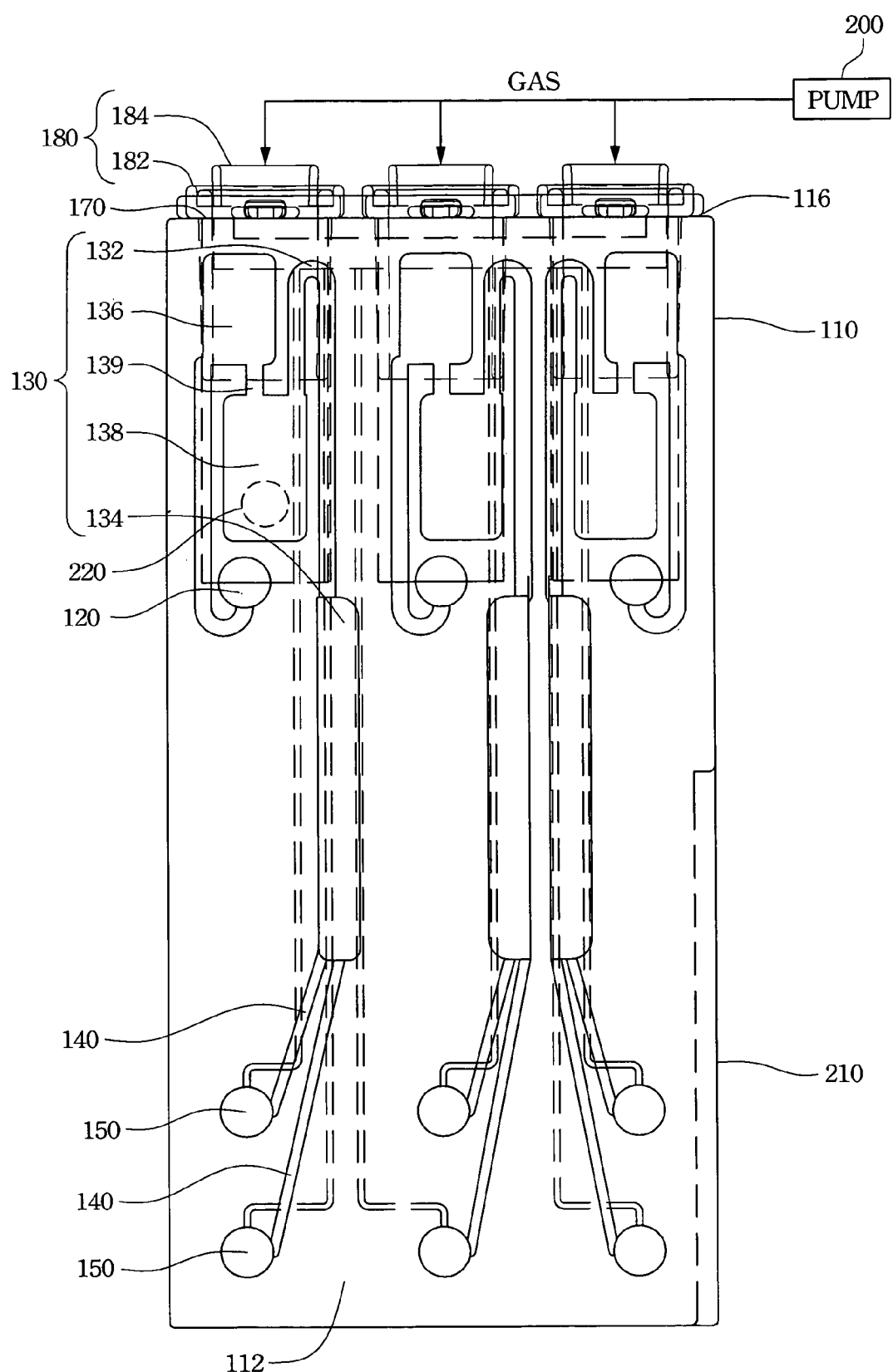
FIG. 1 is a front view of a fluid transferring apparatus according to one embodiment of the present invention.
Figure 2:
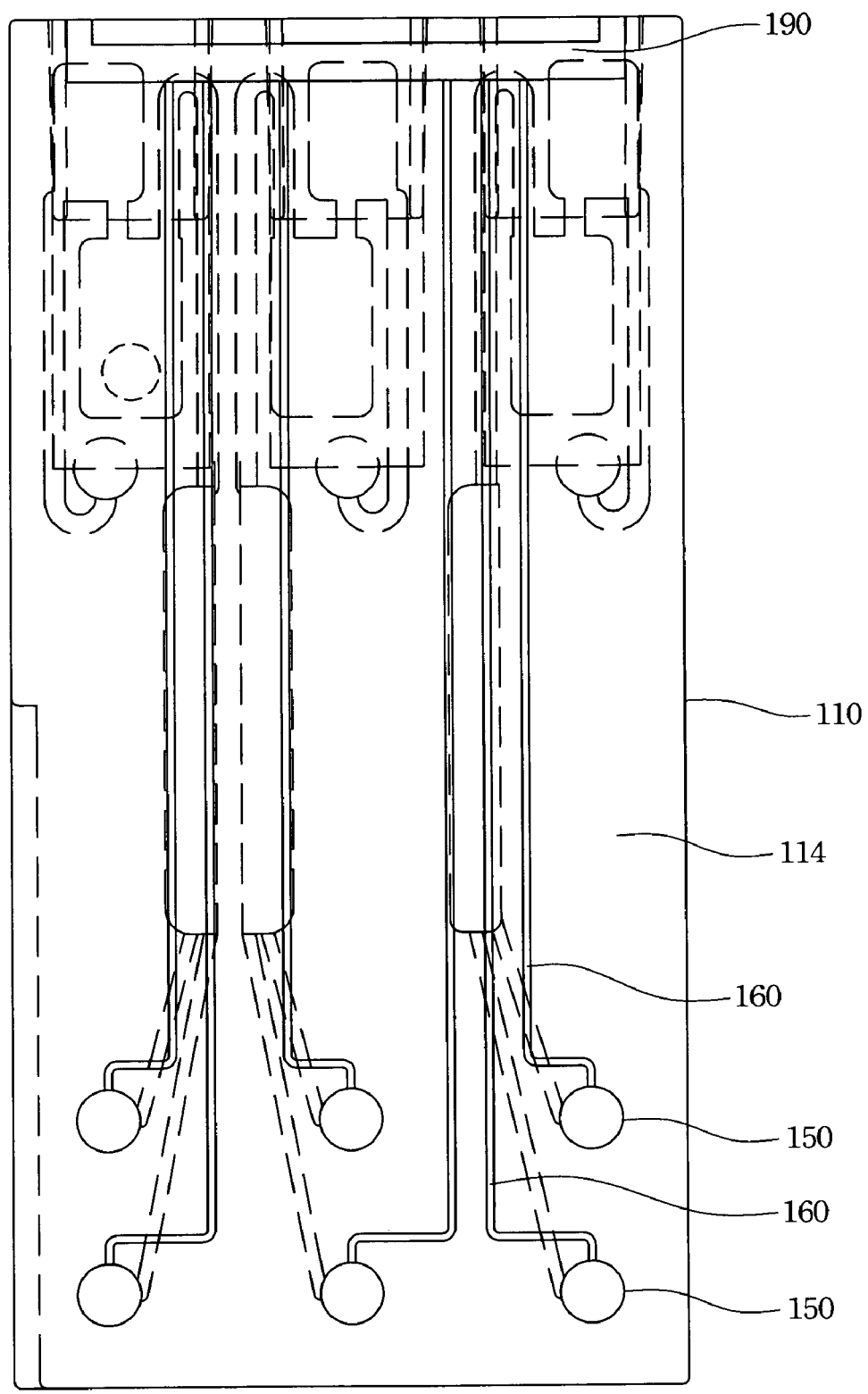
FIG. 2 is a rear view of the frame of FIG. 1.

FIG. 1 is a front view of a fluid transferring apparatus according to one embodiment of the present invention, and FIG. 2 is a rear view of the frame of FIG. 1. As shown in FIGS. 1 and 2, a fluid transferring apparatus includes a frame 110, an sample inlet chamber 120, a filling channel 130, a plurality of filling passageways 140, a plurality of test wells 150, and a plurality of venting passageways 160 (shown in FIG. 2). The sample inlet chamber 120 is disposed within the frame 110. The filling channel 130 is disposed on the frame 110 and connected to the sample inlet chamber 120, wherein the filling channel 130 has a top part 132 above the outlet of the sample inlet chamber 120. The filling passageways 140 are disposed on the frame 110 and connected to the filling channel 130. The test wells 150 are disposed within the frame 110 and connected to the filling passageways 140 respectively, wherein the test wells 150 are below the top part 132 of the filling channel 130. The venting passageways 160 are connected to the test wells 150 respectively.

The term "above" is interpreted "has/have more gravitational potential energy than something else". On the other hand, the term "below" is interpreted "has/have less gravitational potential energy than something else".

More specifically, the opening of the sample inlet chamber 120, the filling channel 130, and the filling passageways 140 may be formed on the front surface 112 of the frame 110. The test wells 150 may pass through the frame 110. The venting passageways 160 may be formed on the rear surface 114 of the frame 110, and the outlet of the venting passageways 160 may be located above the inlet of the filling passageways 140. Furthermore, there may be a transparent film, such as sticky tape, covering the front surface 112 of the frame 110 and the rear surface 114 of the frame 110. It is easily understood that the above-mentioned arrangement is only one example. Other arrangements may also be proper (for example, the venting passageways may be formed on the front surface of the frame).

In use, test reagents and a sample fluid may be put into the test wells 150 and the sample inlet chamber 120 respectively. Then, the pump 200 shown in FIG. 1 is turned on to pump the sample fluid from the sample inlet chamber 120 over the top part 132 of the filling channel 130. Once the sample fluid passes through the top part 132 of the filling channel 130, the pump 200 may be turned off. Then, the sample fluid will flow through the filling passageways 140 into the test wells 150 by gravity to react with the test reagents. Undoubtedly, the timing of when the pump 200 is turned on can be obtained, and the time needed for the sample fluid to pass through the filling channel 130 and the filling passageways 140 can be calculated by fluid mechanics theory. Therefore, the timing of when the sample fluid flows into the test wells 150 can be exactly obtained.

In some cases, the pumping flow of the sample fluid may be unstable due to the mechanism of the pump 200. In order to stabilize the flow of the sample fluid, the filling channel 130 may include at least one filling buffer 134 between the top part 132 of the filling channel 130 and the filling passageways 140. This filling buffer 134 can tolerate the pump instability phenomenon and make sure that once the sample fluid enters into the filling buffer 134, the sample fluid will be driven down by gravity successfully to the test wells 150. The size of the filling buffer 134 should depend on the volume of the sample fluid and the output of the pump 200.

Furthermore, the fluid transferring apparatus of FIG. 1 may include at least one sample fluid inlet 170 disposed on the frame 110 and connected to the sample inlet chamber 120. Particularly, this sample fluid inlet 170 may be located on the top edge 116 of frame 110. In use, the user may drip the sample fluid into the sample fluid inlet 170, and then the sample fluid will be collected in the sample inlet chamber 120 by gravity for the following operations (e.g. pumping).

Figure 3:
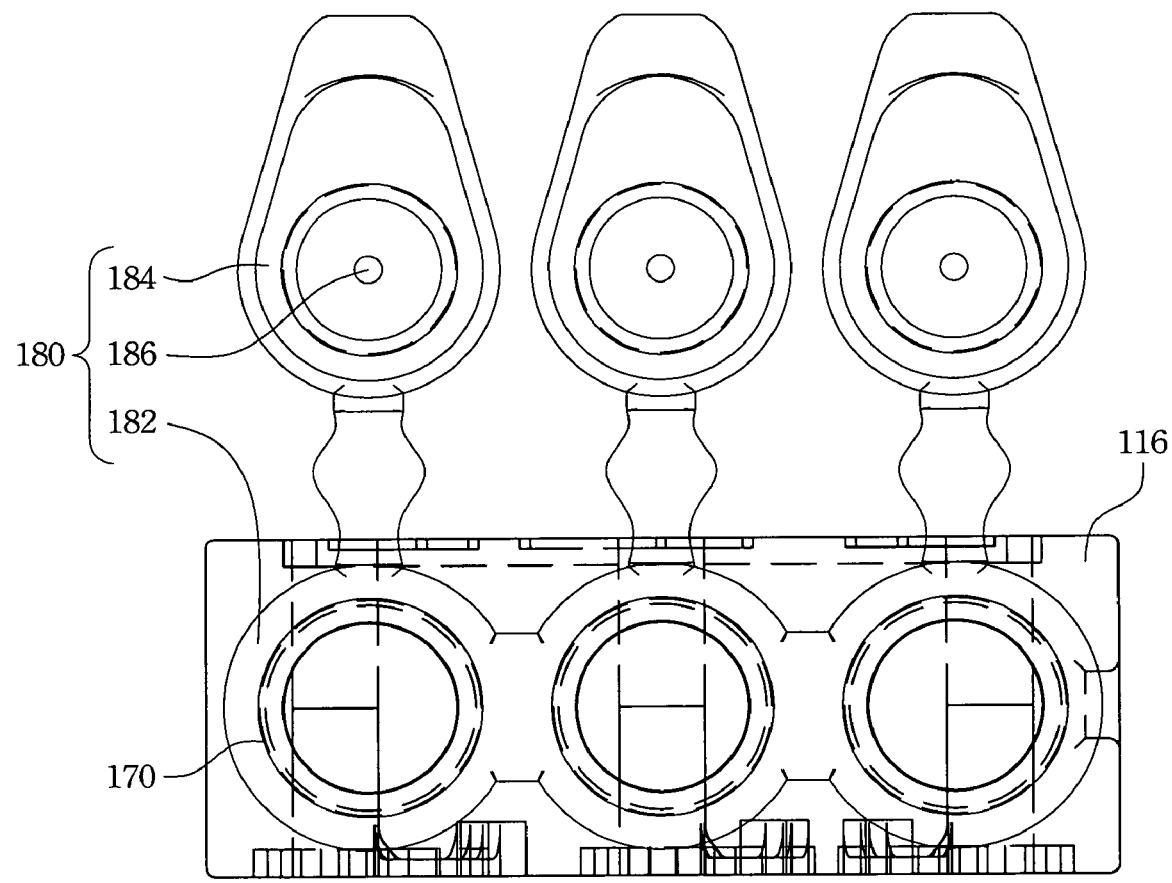
FIG. 3 is a top view of the fluid transferring apparatus of FIG. 1 when the cap is opened.

Furthermore, there may be at least one cap 180 put on the sample fluid inlet 170. FIG. 3 is a top view of the fluid transferring apparatus of FIG. 1 when the cap 180 is opened. The cap 180 may include a body 182 inserted into the sample fluid inlet 170 and a lid 184 connected to the body 182. The lid 184 may have a hole 186 located thereon, such that the pump 200 can inject gas into the sample inlet chamber 120 through the hole 186 to push the sample fluid when pumping. In the present embodiment, the cap 180 may be made of a flexible material, such as polypropylene (PP), to make sure that the connection between the lid 184 and the body 182 can be folded to put the lid 184 on the body 182. Furthermore, this flexibility will allow a tight connection when inserting the cap 180 into the sample fluid inlet 170.

In order to prevent the sample fluid from being pushed into the filling passageways 140 by the action of closing the cap 180, the filling channel 130 may include at least one first inlet buffer 136 between the sample inlet chamber 120 and the top part 132 of the filling channel 130. The capacity of the first inlet buffer 136 should depend on the volume of the sample fluid and the inner volume of the lid 184.

In some cases, the sample fluid may quickly pass through the first inlet buffer 136 without being buffered. In order to fully buffer the sample fluid, the filling channel 130 may further include at least one second inlet buffer 138 between the first inlet buffer 136 and the top part 132 of the filling channel 130. Specifically, the filling channel 130 shown in FIG. 1 may include a shrinking channel 139 connecting the first inlet buffer 136 and the second inlet buffer 138. This shrinking channel 139 can stay the sample fluid in the first inlet buffer 136 and the second inlet buffer 138 to wait for the pumping operation. The size of the shrinking channel 139 should depend on the material of the frame 110.

Referring to FIG. 2, there may be a venting buffer 190 between the venting passageways 160 and the outside of the frame 110. This venting buffer 190 can stop the sample fluid from gushing out to contaminate user space. The capacity of the venting buffer 190 should depend on the volume of the sample fluid.

Referring to FIG. 1, in order to diminish the capillary action of the filling passageways 140, the frame 110 may be made of a hydrophobic material. Accordingly, once the sample fluid enters the filling buffer 134, the sample fluid will be driven down smoothly without interference (bubble) from the capillary action of the filling buffer 134. In the present embodiment, the frame 110 is made of acrylonitrile-butadiene-styrene (ABS) or polymethyl methacrylate (PMMA). It is easily understood that the above-mentioned material is only one example. Other materials, e.g. a hydrophilic material, may also be proper when the sample fluid has to flow fast.

In some cases, the reaction result of the sample fluid with the test reagents may be read by detecting the absorption of visible or ultraviolet light. In order to eliminate the interference of external light, the color of the frame 110 may be black. It is easily understood that the above-mentioned color is only one example. Other colors may be proper as well. For example, the reaction may also be read by the fluorescence or luminescence methods.

Furthermore, there may be a groove 210 located on the side surface of the frame 110. In use, the fluid transferring apparatus may be inserted into an analysis machine, and the groove 210 may match with a protrusion on the analysis machine to make sure that the location of the fluid transferring apparatus in the analysis machine is correct.

In the present embodiment, the frame 110, the sample inlet chamber 120, the filling channel 130, the filling passageways 140, the test wells 150, the venting passageways 160, the sample fluid inlet 170, the venting buffer 190, and the groove 210 may be fabricated by injection molding. Alternatively, the sample inlet chamber 120, the filling channel 130, the filling passageways 140, the test wells 150, the venting passageways 160, the sample fluid inlet 170, the venting buffer 190, and the groove 210 may be formed on the frame 110 by machining. Furthermore, the cap 180 may be fabricated by injection molding as well.

Moreover, the fluid transferring apparatus may further include at least one glass bead 220 restrained in the sample inlet chamber 120. That is, the size of the glass bead 220 is larger than the size of the filling channel 130 so that the glass bead 220 can only stay in the sample inlet chamber 120.

In use, the glass bead 220 may have a first biomolecule coated thereon, and a second biomolecule connected with a labeling molecule is also located in the sample inlet chamber 120. The labeling molecule can be a small molecule such as FITC dye, TRITC dye, or Alexa dyes, or a large molecule such as an enzyme.

When the sample fluid is added into the sample inlet chamber 120, the first and the second biomolecule will bind with the analyte in the sample fluid to form a complex after a suitable reaction time. This complex (with the labeling molecule) and the glass bead 220 will eventually be bound together and thus retained in the sample inlet chamber 120. After the complex formation, the pump pumps the sample fluid into the test wells 150. There is no labeling molecule can be detected in the test wells 150 since the complex (with the labeling molecule) is retained in the sample inlet chamber 120.

However, if there is no analyte in the sample fluid, the second biomolecule (connected with the labeling molecule) will not bind with the glass bead 220 and will be pumped into the test wells 150. As a result, the labeling molecule will be detected in the test wells 150 by absorbance, fluorescence or luminescence methods.

Therefore, the detected signal will be inversely proportional to the analyte amount in the sample fluid and thus quantify the analyte concentration of the sample fluid. When the labeling molecule is an enzyme, the enzyme substrate, which can react with the labeling molecule to result in a detectable signal, may be previously loaded in the test wells 150.

The present embodiment may be used to accomplish the immunoassay of prostate specific antigen (PSA) in a human sample fluid. Where the first biomolecule, coated on the glass bead 220, may be the mouse anti-human PSA antibody. The second biomolecule connected with the labeling molecule may be the horse radish peroxidase (HRP)-labeled goat anti-human PSA antibody. When the PSA analyte is not present in the human sample fluid, the complex will not be formed, and the second biomolecule connected with the labeling molecule can enter the test wells 150 to react with the 3,3',5,5'-tetramethylbenzidine (TMB), which is the HRP substrate. Finally, the color can be detected by absorbance method, and the color signal will has a relationship to the PSA concentration.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A fluid transferring apparatus, comprising:
a frame;
at least one sample inlet chamber disposed within the frame;
at least one filling channel disposed on the frame and connected downstream from the sample inlet chamber, wherein the filling channel has a top part above the outlet of the sample inlet chamber;
a plurality of filling passageways disposed on the frame and connected downstream from the filling channel;
a plurality of test wells disposed within the frame and connected downstream from the filling passageways respectively, wherein the test wells are below the top part of the filling channel; and
a plurality of venting passageways connected downstream from the test wells respectively;
wherein the filling channel comprises at least one filling buffer between the top part of the filling channel and the filling passageways.

2. The fluid transferring apparatus of claim 1, further comprising at least one sample fluid inlet disposed on the frame and connected upstream from the sample inlet chamber.

3. The fluid transferring apparatus of claim 2, further comprising at least one cap put on the sample fluid inlet.

4. The fluid transferring apparatus of claim 3, wherein the filling channel comprises at least one first inlet buffer between the sample inlet chamber and the top part of the filling channel.

5. The fluid transferring apparatus of claim 4, wherein the filling channel comprises at least one second inlet buffer between the first inlet buffer and the top part of the filling channel.

6. The fluid transferring apparatus of claim 5, wherein the filling channel comprises a shrinking channel connecting the first inlet buffer and the second inlet buffer.

7. The fluid transferring apparatus of claim 1, further comprising a venting buffer between the venting passageways and the outside of the frame.

8. The fluid transferring apparatus of claim 1, wherein the frame is made of a hydrophobic material.

9. The fluid transferring apparatus of claim 1, further comprising at least one glass bead restrained in the sample inlet chamber.

10. A fluid transferring apparatus, comprising:
a frame;
at least one sample inlet chamber disposed within the frame;
at least one filling channel disposed on the frame and connected downstream from the sample inlet chamber, wherein the filling channel has a top part above the outlet of the sample inlet chamber;
a pump for pumping a sample fluid from the sample inlet chamber over the top part of the filling channel;
a plurality of filling passageways disposed on the frame and connected downstream from the filling channel;
a plurality of test wells disposed within the frame and connected downstream from the filling passageways respectively, wherein the test wells are below the top part of the filling channel; and
a plurality of venting passageways connected downstream from the test wells respectively.

11. The fluid transferring apparatus of claim 10, wherein the filling channel comprises at least one filling buffer between the top part of the filling channel and the filling passageways.

12. The fluid transferring apparatus of claim 10, further comprising at least one sample fluid inlet disposed on the frame and connected upstream from the sample inlet chamber.

13. The fluid transferring apparatus of claim 12, further comprising at least one cap put on the sample fluid inlet.

14. The fluid transferring apparatus of claim 13, wherein the filling channel comprises at least one first inlet buffer between the sample inlet chamber and the top part of the filling channel.

15. The fluid transferring apparatus of claim 14, wherein the filling channel comprises at least one second inlet buffer between the first inlet buffer and the top part of the filling channel.

16. The fluid transferring apparatus of claim 15, wherein the filling channel comprises a shrinking channel connecting the first inlet buffer and the second inlet buffer.

17. The fluid transferring apparatus of claim 10, further comprising a venting buffer between the venting passageways and the outside of the frame.

18. The fluid transferring apparatus of claim 10, wherein the frame is made of a hydrophobic material.

19. The fluid transferring apparatus of claim 10, further comprising at least one glass bead restrained in the sample inlet chamber.

* * * * *